United States Patent [19]
Chromecek et al.

[11] Patent Number: 5,037,485
[45] Date of Patent: Aug. 6, 1991

[54] METHOD OF CLEANING SURFACES

[75] Inventors: Richard C. Chromecek, Litchfield County, Conn.; Milan F. Sojka, Orange County, N.Y.

[73] Assignee: Dow Corning Corporation, Midland, Mich.

[21] Appl. No.: 407,008

[22] Filed: Sep. 14, 1989

[51] Int. Cl.$^5$ .............................................. B08B 3/00
[52] U.S. Cl. ..................................... 134/7; 134/6; 134/26; 134/30; 134/38; 134/40; 252/158; 252/174.23
[58] Field of Search ................... 134/40, 38, 26, 30, 134/19, 2, 6, 7; 252/158, 174.23

[56] References Cited

U.S. PATENT DOCUMENTS

| | | | |
|---|---|---|---|
| Re. 27,026 | 1/1971 | Alfrey et al. | 260/2.5 |
| 2,809,943 | 10/1957 | Pye et al. | 260/2.1 |
| 3,418,262 | 12/1968 | Werotte et al. | 260/2.2 |
| 3,509,078 | 4/1970 | Roubinek et al. | 260/2.5 |
| 3,627,708 | 12/1971 | Morse et al. | 260/2.5 |
| 3,637,535 | 1/1972 | Corte et al. | 260/2.1 |
| 3,767,600 | 10/1973 | Albright | 260/2.2 |
| 3,989,649 | 11/1976 | Kailto et al. | 260/2.1 |
| 4,208,309 | 6/1980 | Kraemer et al. | 260/8 |
| 4,224,415 | 9/1980 | Meitzner et al. | 521/38 |
| 4,434,067 | 2/1984 | Malone et al. | 252/174.23 |
| 4,537,914 | 8/1985 | Smith et al. | 252/174.23 |
| 4,661,327 | 4/1987 | Horton | 423/7 |
| 4,690,825 | 9/1987 | Won | 424/501 |
| 4,719,040 | 1/1988 | Traas | 512/4 |
| 4,724,240 | 2/1988 | Abrutyn | 514/847 |
| 4,764,362 | 8/1988 | Barchas | 424/61 |
| 4,776,358 | 10/1988 | Korsk | 132/321 |
| 4,785,060 | 11/1988 | Nagler | 252/174.23 |
| 4,806,360 | 2/1989 | Leong | 424/487 |
| 4,813,976 | 3/1989 | Barchas | 51/293 |
| 4,828,542 | 5/1989 | Hermann | 604/3 |
| 4,908,149 | 3/1990 | Moore et al. | 252/174.23 |

FOREIGN PATENT DOCUMENTS

| | | |
|---|---|---|
| 1168157 | 5/1984 | Canada . |
| 61701 | 10/1982 | European Pat. Off. . |
| 0252463 | 1/1988 | European Pat. Off. . |
| 0306236 | 3/1989 | European Pat. Off. . |
| 2608533 | 9/1976 | Fed. Rep. of Germany . |
| 8801164 | 2/1988 | PCT Int'l Appl. . |
| 8702389 | 9/1987 | South Africa . |

*Primary Examiner*—Asok Pal
*Attorney, Agent, or Firm*—Jim L. DeCesare

[57] ABSTRACT

This invention relates to a process of cleaning a surface soiled with a staining agent. The method includes the steps of applying to the soiled surface a highly crosslinked macroporous hydrophobic copolymer which contains a chemical entrapped therein which is a solvent for the staining agent present on the soiled surface, dissolving the staining agent with the solvent, absorbing the staining agent into the solvent entrapped copolymer, and removing the copolymer containing the solvent and the dissolved staining agent from the surface.

11 Claims, 6 Drawing Sheets

1500X

10000X

2000X

1500X

10000X 1000X
0 RPM
⊢——⊣ 10 μm 1000X
75 RPM
⊢——⊣ 10 μm 1000X
150 RPM
⊢—⊣ 10 μm 1000X
300 RPM
⊢—⊣ 10 μm

METHOD OF CLEANING SURFACES

BACKGROUND OF THE INVENTION

This invention relates to a method of cleaning surfaces with the aid of macroporous cross-linked copolymers. More particularly, the invention includes the concept of conducting the process in the presence of a solvent and rubbing into the surface to be cleaned the copolymer containing the solvent.

The concept of producing spheres or beads by means of suspension polymerization techniques is well known in the prior art. An exemplary one of such processes is disclosed in U.S. Pat. No. 2,809,943, issued Oct. 15, 1957. However, it was found that when a material was added which is a solvent for the monomers, but acts as a precipitant for the resulting polymer, a novel form of bead was provided containing a network of microscopic channels. This discovery is set forth in U.S. Pat. No. 4,224,415, filed July 18, 1958, issuing some twenty-two years later on Sept. 23, 1980. In this patent, beads are produced ranging in size from about 350 to about 1200 microns. Typical monomers include divinyl toluene, diallyl maleate, and triallyl phosphate. The precipitant employed is an alkane, acid ester, or alcohol.

This technology was expanded and the precipitant was variously described in the patent literature as a diluent, porogen, active ingredient, solvent, functional material, and volatile agent. For example, in U.S. Pat. No. Re. 27,026, issued Jan. 12, 1971, porous beads of a diameter less than ten microns are disclosed. Among the monomers used to produce the beads are ethyl methacrylate, divinyl benzene, and ethylene glycol dimethacrylate. In U.S. Pat. No. 3,418,262, issued Dec. 24, 1968, there is described a bead characterized as having a rigid sponge structure, and wherein the porogenic agent employed is an acid such as stearic acid. Intermediates in bead form were produced in U.S. Pat. No. 3,509,078, issued Apr. 28, 1970, using polymeric materials such as polyethylene glycols as the precipitant material during the in situ suspension polymerization process. The macroporous character of such bead construction is graphically portrayed and illustrated in FIG. 1 of U.S. Pat. No. 3,627,708, issued Dec. 14, 1971. Beads termed "pearls" are produced, and containing active ingredients therein such as water or various alcohol ethers. The pearls are crosslinked to the extent of about twenty percent. In U.S. Pat. No. 3,637,535, issued Jan. 25, 1972, beads with a sponge structure are said to be capable of being compressed to an imperceptible powder. These beads are capable of being loaded with as much as 200-300% of active ingredients such as white spirit, and benzin. A rigid porous bead of a trifunctional methacrylate is taught in U.S. Pat. No. 3,767,600, issued Oct. 23, 1973. Such beads have a size of 10-900 microns, and various other monomers which can be employed include diacetone acrylamide, and ethylhexyl, hydroxyethyl, and hydroxypropyl methacrylates. Paraffin wax in an amount of 5-100% is used to form the microscopic network of channels in U.S. Pat. No. 3,989,649, issued Nov. 2, 1976. The wax may be removed from the bead structure by solvent extraction.

While many of the foregoing U.S. patents relate to ion exchange technology, a bead similar to those previously described is employed as a carrier for enzymes in U.S. Pat. No. 4,208,309, issued June 17, 1980. Such beads are of the size of about 0.1 mm. U.S. Pat. No. 4,661,327, issued Apr. 28, 1987, describes a macroreticular bead containing a magnetic core. The use of hard crosslinked porous polymeric beads in cosmetics as carriers is taught in U.S. Pat. No. 4,724,240, issued Feb. 9, 1988, wherein various emollients and moisturizers are entrapped therein. These beads are said to be capable of entrapping materials such as 2-ethylhexyl oxystearate, arachidyl propionate, petroleum jelly, mineral oil, lanolin, and various siloxanes. The size of the beads ranges from 1-3,000 microns. Typical monomers include ethylene glycol dimethacrylate, lauryl methacrylate, trimethylol propane trimethacrylate, and dipentaerythritol dimethacrylate. "In situ" hydrophobic powders and "in situ" beads may be produced in accordance with the teaching of this patent. Beads having a rigid sponge structure are also described in U.S. Pat. No. 4,690,825, issued Sept. 1, 1987, and wherein the beads function as a delivery vehicle for a host of materials including pigments, vitamins, fragrances, drugs, repellants, detergents, and sunscreens. The beads have a size of 10-100 microns and are preferably of a monomer system of styrene-divinyl benzene. Crosslinking is said to range from 10-40 percent. U.S. Pat. No. 4,806,360, issued Feb. 21, 1989, describes a post adsorbent bead which contains a melanin pigment for use as a sunscreen.

The foreign patent literature includes West German Offenlegungsschrift No. P-2608533.6, published Sept. 30, 1976, and wherein porous polymeric beads produced by "in situ" suspension polymerization are provided, and which are adapted to release perfumes. A controlled release of the fragrance is disclosed, providing utility for such beads in the home, automobiles, airplanes, railway cars, hospitals, classrooms, conference centers, and gymnasiums. Canadian Patent No. 1,168,157, issued May 29, 1984, describes hard, discrete, free flowing, bead constructions in which the beads entrap a series of functional materials which can be incorporated into toilet soap, body powder, and antiperspirant sticks. The Canadian Patent, it is noted, is the equivalent of European Patent No. 61,701, issued on July 16, 1986, both of which are foreign equivalents of the parent case of the '240 patent. In European International Publication No. 0252463A2, published Jan. 13, 1988, there is disclosed a bead having a hydrophobic polymer lattice, and which entraps numerous non-cosmetic materials such as pesticides, pharmaceuticals, pheromones, and various categories of chemicals. Steroids are entrapped, for example, in the porous beads of PCT International Publication No. WO-88/01164, published on Feb. 25, 1988. The steroids are adrenocortical steroids or various anti-inflammatory type steroids. It should therefore be apparent that what began as a simple ion exchange bead concept has rapidly grown into a technology of widely varied application.

In accordance with the present invention, copolymer powders are employed in novel processes not believed to be taught in the prior art, as exemplified by the foregoing patents. Those patents, in general, relate to suspension polymerization processes for the production of porous polymeric and copolymeric spheres and beads in which the precipitant is present during polymerization. These are defined as an "in situ" process.

Thus, according to the prior art, crosslinked porous copolymers in particle form can be produced by at least three distinct processes. One process produces beads by "in situ" suspension polymerization. Another process produces beads by suspension polymerization but the beads are "post adsorbed" with an active ingredient after the volatile porogen is removed. In a third process, powders are produced by "in situ" precipitation polymerization.

What has been accomplished in accordance with the present invention, however, is a unique concept differing from all of the foregoing methods, and wherein post adsorbent powders and beads are produced and used in a novel fashion.

SUMMARY OF THE INVENTION

This invention relates to a process of cleaning a surface soiled with a staining agent. The method includes the steps of applying to the soiled surface a highly cross-linked macroporous hydrophobic copolymer which contains a chemical entrapped therein which is a solvent for the staining agent present on the soiled surface, dissolving the staining agent with the solvent, absorbing the staining agent into the solvent entrapped copolymer, and removing the copolymer containing the solvent and the dissolved staining agent from the surface.

In certain of the more specific embodiments of the present invention, one monomer of the copolymer is a monounsaturated monomer and the monounsaturated monomer is lauryl methacrylate. One monomer of the copolymer can also be a polyunsaturated monomer and the polyunsaturated monomer is selected from the group consisting of ethylene glycol dimethacrylate and tetraethylene glycol dimethacrylate.

The copolymer is in the form of a powder and the powder is a combined system of particles, the system of particles including unit particles of less than about one micron in average diameter, agglomerates of fused unit particles of sizes in the range of about twenty to eighty microns in average diameter, and aggregates of clusters of fused agglomerates of sizes in the range of about two-hundred to about twelve-hundred microns in average diameter. The soiled surface can be a textile in which case the copolymer containing the solvent is pressed and rubbed into the textile surface after being applied to the surface. The solvent is evaporated from the copolymer following removal of the copolymer containing the solvent and the staining agent from the surface, and the solvent free copolymer containing the staining agent is discarded.

The copolymer containing the solvent and the staining agent can be removed from the surface by brushing the surface, followed by the application of pressurized air to the brushed surface. The staining agent may be butter, grass, and motor oil and the soiled surface treated in accordance with the present invention could be wool, paper, cotton, silk, rayon, linen, and polyester. The solvent is preferably heptane, methylene chloride, and ethyl alcohol, although other appropriate solvents may be employed.

The invention is also directed to a more simplified process in which no solvent is employed. In this case, the steps are related to a process of cleaning a surface soiled with a staining agent by applying to the soiled surface a highly cross-linked macroporous hydrophobic copolymer, rubbing and mixing the copolymer into the staining agent on the soiled surface, absorbing the staining agent into the copolymer, and removing the copolymer containing the staining agent from the surface. The staining agent is, for example, grease, lipid deposits, and plaque, while the soiled surface may be glass, spectacle lenses, and dentures. The copolymer containing the staining agent is removed from the surface by flushing the surface with water.

A precipitation polymerization process is used for producing the macroporous cross-linked copolymer. In the process, there is copolymerized at least one monounsaturated monomer and at least one polyunsaturated monomer in the presence of an organic liquid which is a solvent for and dissolves the monomers but not the copolymer. The copolymerization of the monomers is initiated by means of a free radical generating catalytic compound, precipitating a copolymer in the solvent in the form of a powder. A dry powder is formed by removing the solvent from the precipitated copolymeric powder.

The solvent is preferably isopropyl alcohol, although ethanol, toluene, heptane, xylene, hexane, ethyl alcohol, and cyclohexane, may also be employed. The monounsaturated monomer and the polyunsaturated monomer can be present in mol ratios of, for example, 20:80, 30:70, 40:60, or 50:50. The process includes the step of stirring the monomers, solvent, and the free radical generating catalytic compound, during copolymerization. Preferably, the dry powder is formed by filtering excess solvent from the precipitated powder, and the filtered powder is vacuum dried. The powder may then be "post adsorbed" with various functional materials.

The powders of the present invention may be used as carriers or adsorbents for materials such as water, aqueous systems, emollients, moisturizers, fragrances, dyes, pigments, flavors, drugs such as ibuprofen, phosphoric acid, insect repellents, vitamins, sunscreens, detergents, cosmetics, pesticides, pheromones, herbicides, steroids, sweeteners, pharmaceuticals, and antimicrobial agents. Finely divided solids such as analgesic materials can be adsorbed by dissolving the finely divided analgesic in a solvent, mixing the analgesic and solvent with the powder, and removing the solvent. Other post adsorbable materials include alkanes, alcohols, acid esters, silicones, glycols, organic acids, waxes, and alcohol ethers.

These and other objects, features, and advantages, of the present invention will become apparent when considered in light of the following detailed description, including the accompanying drawings.

IN THE DRAWINGS

Figure 1:
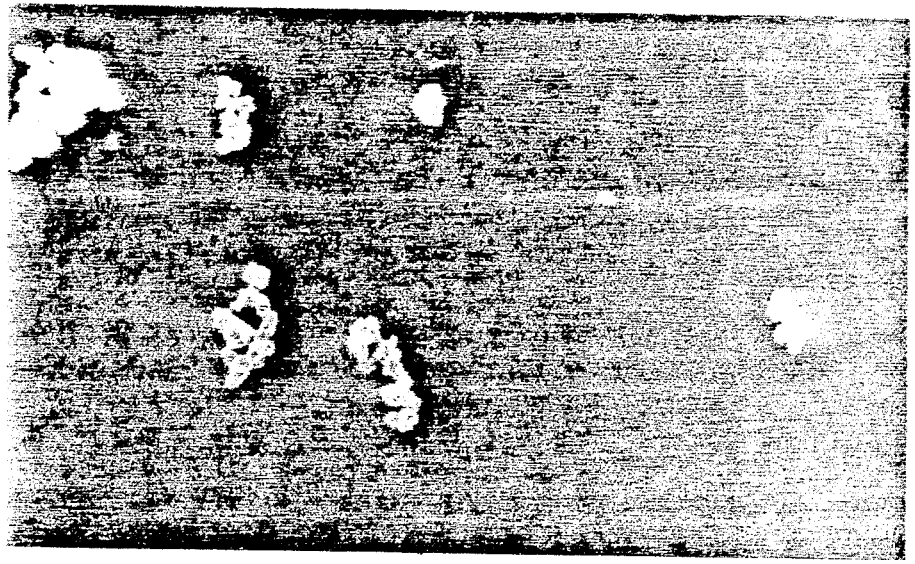
FIG. 1 is a photomicrograph of the various components of the complex structure of the powder produced in Example I, and including unit particles, agglomeratures, and aggregates.
Figure 2:
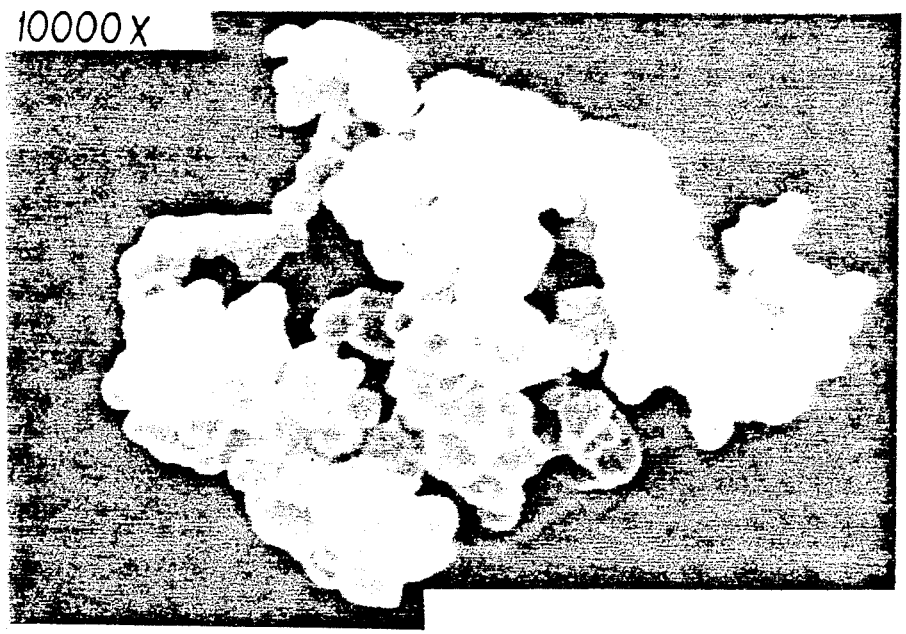
FIGS. 2 and 3 are photomicrographs of the agglomerates and aggregates of FIG. 1, respectively, shown on a larger scale.
Figure 3:
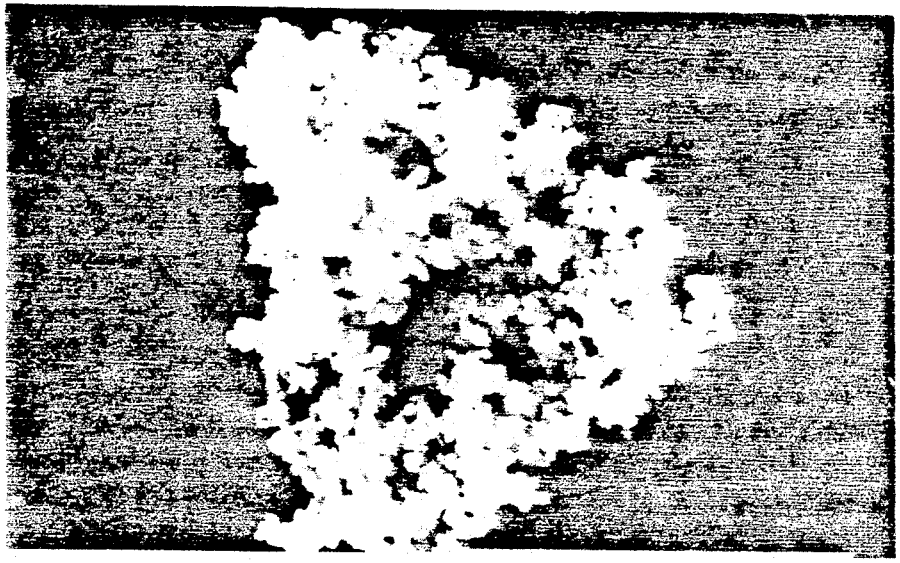

In the above figures in the drawing, the magnification is indicated in each instance. For example, the magnification in FIGS. 6-9 is 1000×, and 2000× in FIG. 10. FIGS. 6-10 also include an insert identifying a length approximating ten microns for comparative purposes.

It should be pointed out, that in viewing the various figures, one will note that as the rate of stirring is increased from zero rpm up to eight hundred rpm, that the size of the unit particles increase. This is in direct opposition to what has been traditionally observed in suspension polymerization systems, wherein increases in stirring rates decrease particle size. Because of the increased size of the unit particles shown in FIG. 10 and the resulting decrease in surface area, the adsorptive capacity of these large particles is less than the adsorptive capacity of the smaller sized particles shown in FIGS. 6-9.

The most effective unit particles can be produced if the rate of stirring is maintained below about three hundred rpm, although particles produced at rates beyond three hundred rpm are useful and adsorptive, but to a lesser extent.

DETAILED DESCRIPTION OF THE INVENTION

The material of the present invention, can be broadly and generally described as a crosslinked copolymer capable of entrapping solids, liquids, and gases. The copolymer is in particulate form and constitutes free flowing discrete solid particles even when loaded with an active material. When loaded, it may contain a predetermined quantity of the active material. One copolymer of the invention has the structural formula:

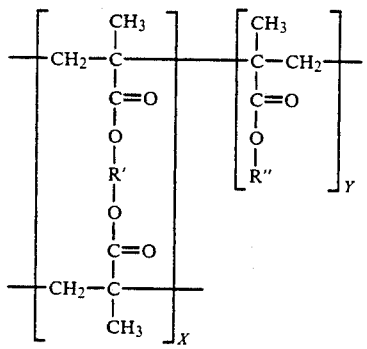

where the ratio of x to y is 80:20, R' is $-CH_2CH_2-$, and R" is $-(CH_2)_{11}CH_3$.

The copolymer is highly crosslinked as evidenced by the foregoing structural formula, and is more particularly a highly crosslinked polymethacrylate copolymer. This material is manufactured by the Dow Corning Corporation, Midland, Mich., U.S.A., and sold under the trademark POLYTRAP®. It is a low density, highly porous, free-flowing white particulate, and the particles are capable of adsorbing high levels of lipophilic liquids and some hydrophilic liquids, while at the same time maintaining a free-flowing particulate character.

In the powder form, the structure of the particulate is complex, and consists of unit particles less than one micron in average diameter. The unit particles are fused into agglomerates of twenty to eighty microns in average diameter. These agglomerates are loosely clustered into macro-particles termed aggregates of about 200 to about 1200 microns in average diameter.

Adsorption of actives to form post adsorbent powder, can be accomplished using a stainless steel mixing bowl and a spoon, wherein the active ingredient is added to the empty dry powder, and the spoon is used to gently fold the active into the powder. Low viscosity fluids may be adsorbed by addition of the fluids to a sealable vessel containing the powder and tumbling the materials until a consistency is achieved. More elaborate blending equipment such as ribbon or twin cone blenders can also be employed.

The following example illustrates the method for making a post adsorbent powder, of the type illustrated in FIGS. 1-3 and 6-10.

EXAMPLE I

A hydrophobic porous copolymer was produced by the precipitation polymerization technique by mixing in a five hundred milliliter polymerization reactor equipped with a paddle type stirrer, 13.63 grams of ethylene glycol dimethacrylate monomer, or eighty mole percent, and 4.37 grams of lauryl methacrylate monomer, or twenty mole percent. Isopropyl alcohol was added to the reactor as the solvent in the amount of 282 grams. The monomers were soluble in the solvent, but not the precipitated copolymer. The process can be conducted with only polyunsaturated monomers if desired. The mixture including monomers, solvent, and 0.36 grams of catalytic initiator benzoyl peroxide, was purged with nitrogen. The system was heated by a water bath to about sixty degrees Centigrade until copolymerization was initiated, at which time, the temperature was increased to about 70-75 degrees Centigrade for six hours, in order to complete the copolymerization. During this time, the copolymer precipitated from the solution. The copolymerization produced unit particles of a diameter less than about one micron. Some of the unit particles adhered together providing agglomerates of the order of magnitude of about twenty to eighty microns in diameter. Some of the agglomerates adhered further and were fused and welded one to another, forming aggregates of loosely held assemblies of agglomerates of the order of magnitude of about two to eight hundred microns in diameter. The mixture was filtered to remove excess solvent, and a wet powder cake was tray dried in a vacuum oven. A dry hydrophobic copolymeric powder consisting of unit particles, agglomerates, and aggregates was isolated.

The adsorptive capacity of the hydrophobic particulates produced in Example I, as a function of the stirring rate, was determined. The stirring rate during the reaction in Example I significantly influenced the adsorption properties of the particulate materials. The adsorptivity of the particulate materials decreases with an increase in stirring rate, and the density of the particulates increases. These results are set forth in Tables I-III.

TABLE I

| Agitation Rate (RPM) | Bulk Density Size (g/cc) | Average Aggregate Size (μ) | Average Agglomerate Size (μ) | Average Unit Particle Size (μ) | Adsorption Capacity* |
|---|---|---|---|---|---|
| 0 | 0.067 | 182.5 | 33.9 | 1.0 | 83.0 |

TABLE I-continued

| Agitation Rate (RPM) | Bulk Density Size (g/cc) | Average Aggregate Size (μ) | Average Agglomerate Size (μ) | Average Unit Particle Size (μ) | Adsorption Capacity* |
|---|---|---|---|---|---|
| 75 | 0.077 | 140.6 | 36.6 | 0.5 | 84.8 |
| 150 | 0.071 | 149.8 | 39.8 | 0.8 | 83.0 |
| 300 | 0.293 | 47.0 | 34.0 | 1.5–2.0 | 58.3 |
| 800 | 0.440 | — | 10.0 | 3.0–5.0 | 37.7 |

\* = Percent Silicone Oil

TABLE II

| Stirring Speed RPM | Adsorption Capacity % | | | |
|---|---|---|---|---|
| | Water | Mineral Oil | Glycerine | Organic Ester* |
| 0 | 0 | 80 | 75 | 80 |
| 75 | 0 | 83.9 | 75 | 81.5 |
| 150 | 0 | 80 | 75 | 80 |
| 300 | 0 | 54.5 | 58.3 | 54.5 |

\* = 2-ethylhexyl-oxystearate

TABLE III

| RPM | Adsorption Capacity % | | | Density (g/cm³) | |
|---|---|---|---|---|---|
| | Mineral Oil | 2-ethylhexyl oxystearate | Silicone Oil | Bulk | Tapped |
| 0 | 82.5 | 82.5 | 86.5 | 0.0368 | 0.0580 |
| 75 | 82.3 | 82.2 | 86.5 | 0.0462 | 0.0667 |
| 150 | 82.3 | 82.3 | 86.3 | 0.0527 | 0.0737 |
| 200 | 81.5 | 81.5 | 85.7 | 0.0554 | 0.0752 |
| 250 | 79.2 | 80.0 | 84.8 | 0.0636 | 0.0859 |
| 300 | 68.8 | 68.8 | 75.0 | 0.1300 | 0.1768 |
| 450 | 58.3 | 58.3 | 61.5 | 0.1736 | 0.2392 |
| 600 | 54.5 | 54.5 | 60 | 0.1933 | 0.2792 |
| 700 | 42.2 | 42.5 | 45.7 | 0.2778 | 0.4142 |
| 800 | 33.3 | 28.6 | 33.3 | 0.3862 | 0.5322 |
| 1000 | 32.8 | 28.5 | 32.9 | 0.3808 | 0.5261 |

In the foregoing tables, it can be seen that adsorption and density, as a function of stirring rate, was determined for several fluids including a silicone oil, water, mineral oil, glycerine, and an organic ester. From zero rpm up to about 250 rpm, the adsorptivity of the porous copolymeric powder particulates of Example I remained essentially consistent. However, at about three hundred rpm, there was a substantial decrease in adsorptivity, which decrease became more apparent as the stirring rate was increased up to about one thousand rpm. A similar pattern is evidenced by the data which are reflective of the density.

This phenomenon is more apparent in the photomicrographic figures of the drawing. Thus, it can be seen from FIG. 6, that the particle size of the unit particles increases as the stirring rate is increased, as evidenced by FIG. 10. A progression in this phenomenon can be observed in FIGS. 7–9.

While the procedure of Example I is a precipitation polymerization process and not a suspension polymerization system, the prior art dealing with suspension polymerization processes, teaches that an increase in stirring rate causes a decrease in particle size. This is documented, for example, in U.S. Pat. No. 4,224,415, issued Sept. 23, 1980, and in the PCT International Publication. The PCT International Publication employs stirring rates upwards of nine hundred to twelve hundred rpm. In Example I of the present invention, however, increases in stirring rates not only did not decrease the particle size, but in fact had exactly the opposite effect, causing the unit particle size to increase. As the rate of stirring increased from zero rpm up to one thousand, the density of the particles increased and the adsorptive capacity decreased.

In accordance with the above, it is possible to tailor porous adsorbent powders of a particular particle size and adsorptivity by means of stirring rate. Thus, with large unit particles in FIG. 10, the adsorptive capacity is less than the adsorptive capacity of smaller sized unit particles in FIGS. 6–9. While the most effective particles are produced when the rate of stirring is maintained below about three hundred rpm, particles produced at rates beyond three hundred rpm are useful.

Figure 4:
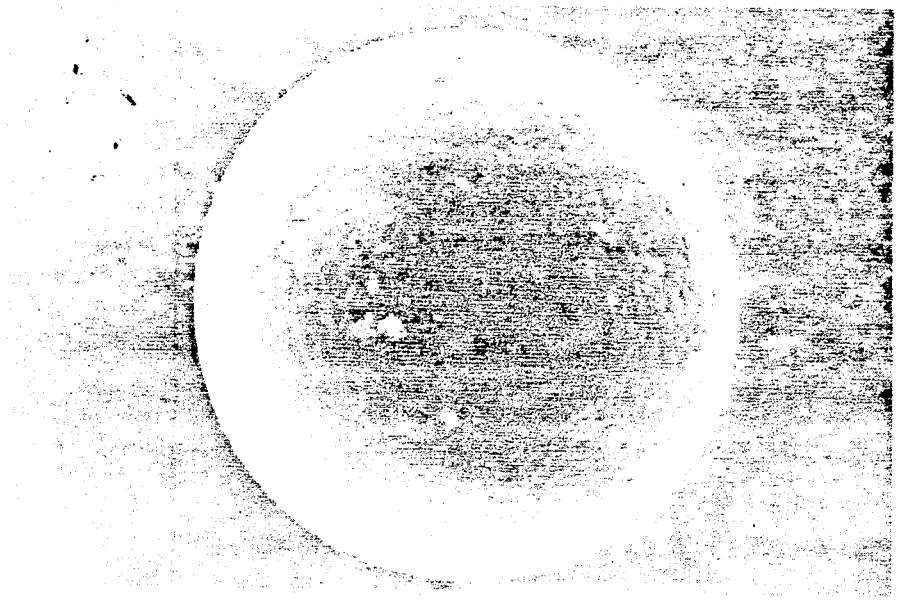
FIG. 4 is a photomicrograph of a polymer bead produced by suspension polymerization.
Figure 5:
FIG. 5 is a photomicrograph of the bead of FIG. 4 with a portion of the shell removed to reveal the interior structure of the bead.
Figure 6:
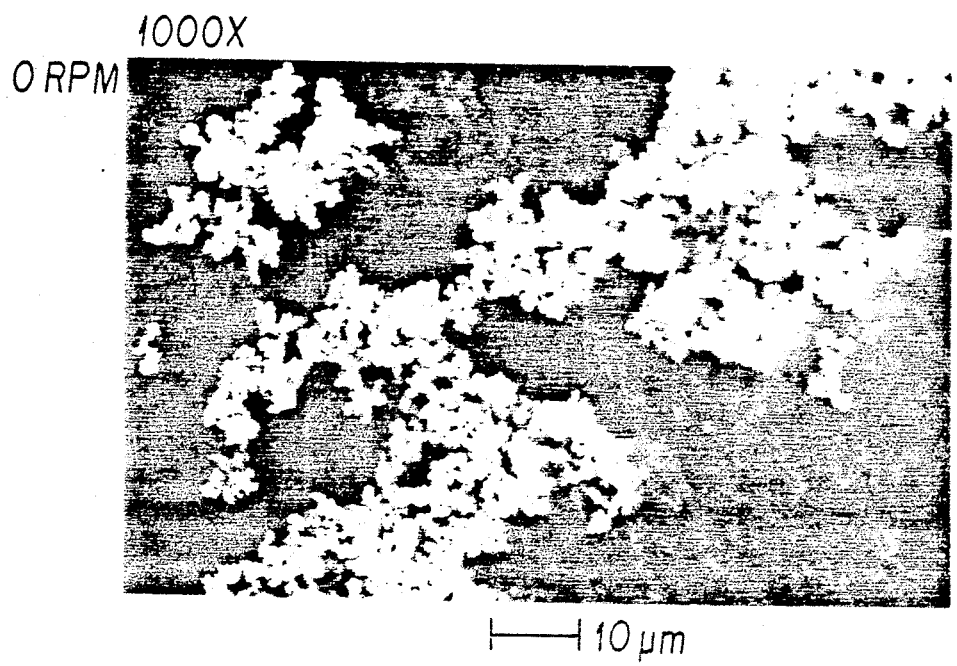
FIG. 6 is a photomicrograph of a copolymeric powder material. The powder is shown in magnification as it appears when the agitation rate employed in the process for producing the powder is zero rpm.
Figure 7:
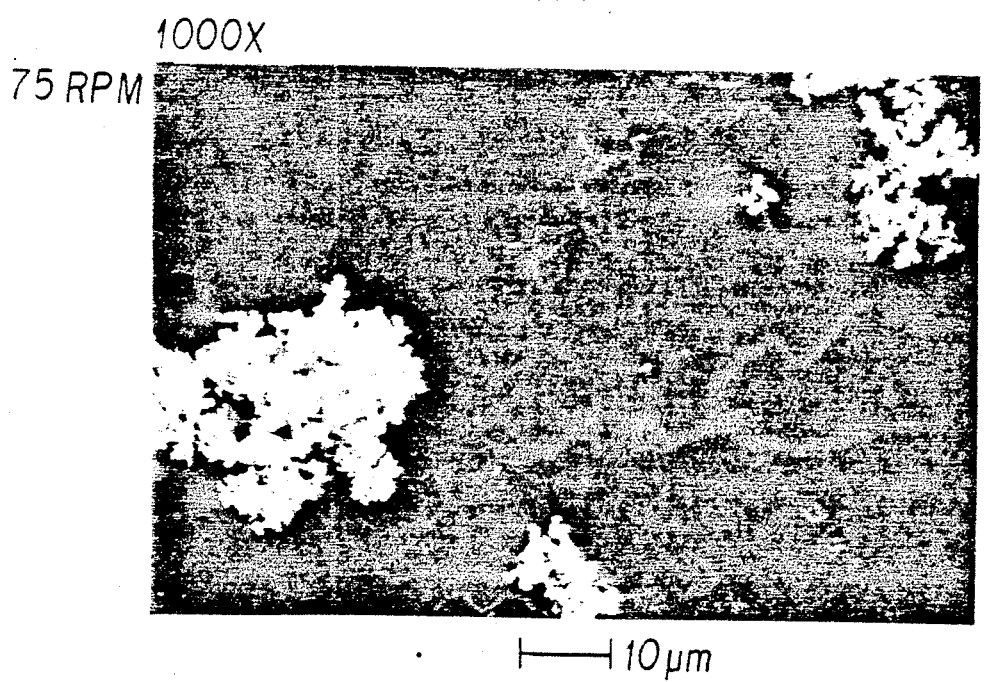
FIGS. 7-10 are additional photomicrographs of copolymeric powder materials. The powder is shown in magnification as it appears when the agitation rate employed in the process for producing the powder varies from seventy-five rpm up to eight hundred rpm.
Figure 8:
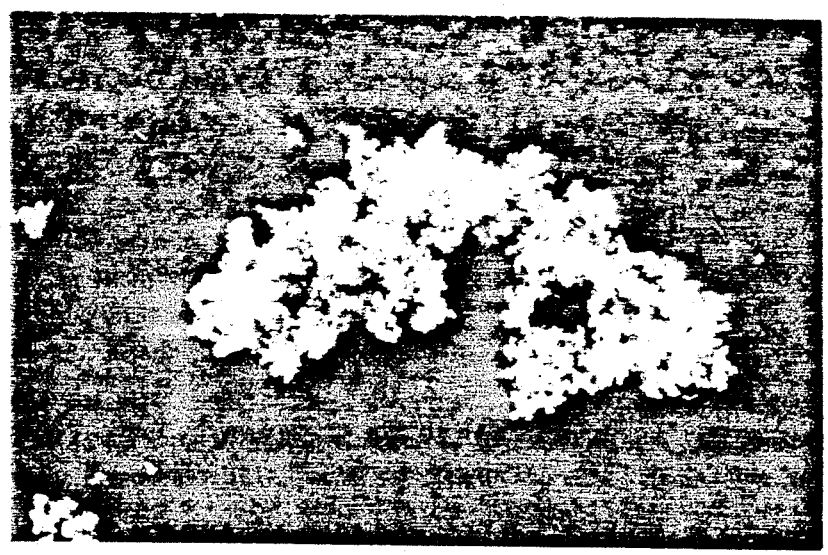
Figure 9:
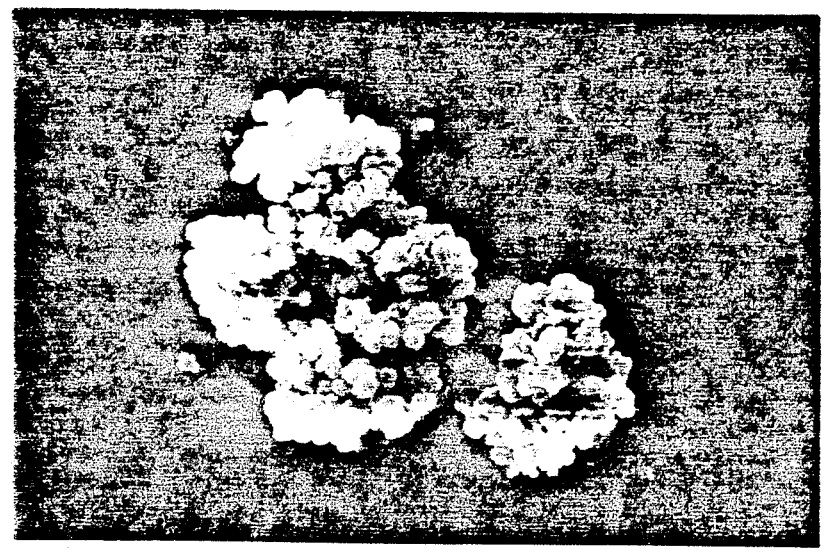
Figure 10:
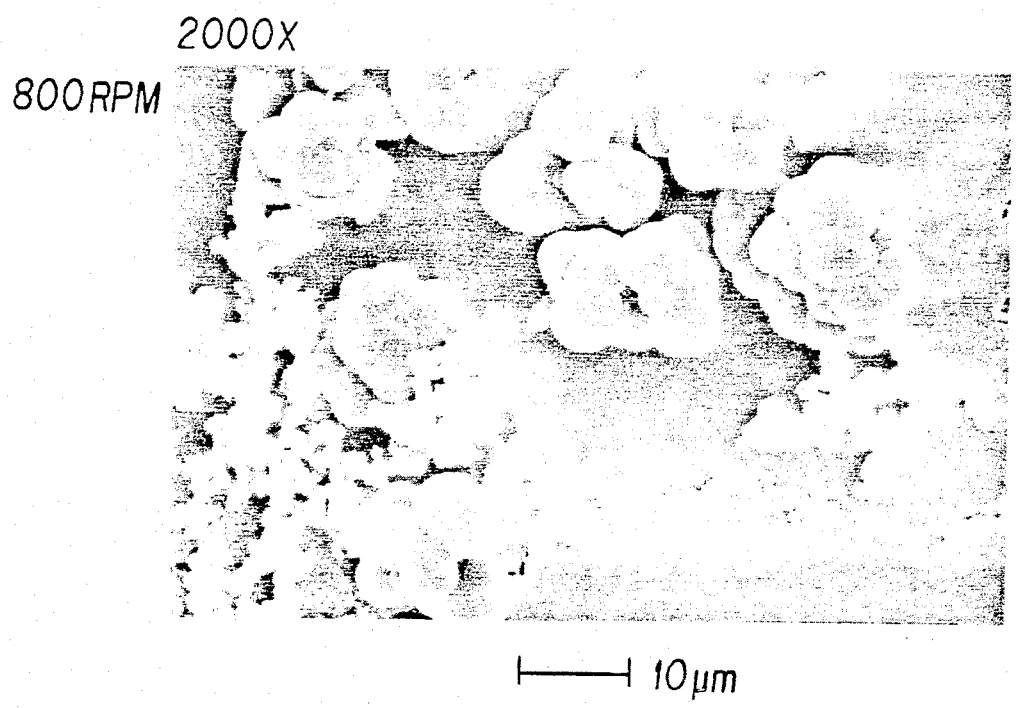

It is important to understand that the method of Example I for the production of porous copolymer particulate powder materials is characterized as a precipitation polymerization technique. In accordance with the technique, monomers are dissolved in a compatible volatile solvent in which both monomers are soluble. Polymer in the form of a powder is precipitated and the polymer is insoluble in the solvent. No surfactant or dispersing aid is required. The materials produced are powders and not spheres or beads. The powder particulates include unit particles, agglomerates, and aggregates. The volatile solvent is subsequently removed resulting in a dry powder, which can be post adsorbed with a variety of functional active ingredients. The suspension polymerization process on the other hand, provides that polymerization be carried out in water, and in some cases chloroform or chlorinated solvents. The monomers, the active, and the catalyst, form beads or droplets in water, and polymerization occurs within each bead. A surfactant or stabilizer, such as polyvinyl pyrrolidone, is required in order to prevent the individually formed beads and droplets from coalescing. The resulting beads, with the active material entrapped therein, include a substantially spherical outer crust or shell, the interior of which contains a macroporous structure of fused unit particles, agglomerates, and aggregates. The bead is about ten microns in average diameter to about one hundred-fifty microns, depending upon the rate of agitation employed during the process. Such beads are shown in FIGS. 4 and 5, and the process is set forth in Example III.

Some unique features of the powders of Example I and FIGS. 1–3 and 6–10 are their ability to adsorb from sixty to eighty percent of a liquid and yet remain free flowing. The materials provide a regulated release of volatile ingredients such as cyclomethicone entrapped therein, and have the capability of functioning as carriers for other non-volatile oils. Loaded powders disappear when rubbed upon a surface. This phenomenon is believed due to the fact that large aggregates of the material scatter light rendering the appearance of a white particulate, however, upon rubbing, these large aggregates decrease in size approaching the range of visible light and hence seem to disappear. The materials find applications in diverse areas such as cosmetics and toiletries, household and industrial products, pesticides, pheromone carriers, and pharmaceuticals. The materials do not swell in common solvents and are capable of physically adsorbing active ingredients by the filling of interstitial voids by capillary action. The active ingredients are subsequently released by capillary action or wicking from the voids within the particulates.

The following example illustrates a precipitation polymerization process in which an organic ester is entrapped "in situ" in the polymer powder.

EXAMPLE II 7 grams of 2-ethylhexyl oxystearate was mixed with 1.5 grams of ethylene glycol dimethacrylate and 1.5 grams of lauryl methacrylate in a glass test tube. The solution was deaerated for five (5) minutes and 0.1 ml of t-butyl peroctoate was added and mixed while heating to 80 degrees Centigrade in an oil bath. After 20 minutes, the contents solidified; and the mixture was maintained at about 80 degrees Centigrade for an additional hour to assure full polymerization. A semi-soft, heterogeneous white opaque polymer mass resulted containing the entrapped ester.

The powder of Example II differs from the powder of Example I in that the solvent in Example I is removed resulting in a dry empty powder which is post adsorbed with other functional materials. The powder of Example II is otherwise similar to the material shown in FIGS. 1-3.

Example III illustrates a process for the production of beads as shown in FIGS. 4 and 5. The process is suspension polymerization and an organic ester is entrapped "in situ".

EXAMPLE III 1.20 grams of polyvinyl pyrrolidone was dissolved in 1500 ml of water in a 2000 ml three necked resin flask equipped with a stirrer, thermometer and nitrogen purge. A solution of 335 grams of 2-ethylhexyl oxystearate, 132 grams ethylene glycol dimethacrylate, 33 grams 2-ethylhexyl methacrylate, and 5 ml t-butyl peroctoate, was bubbled with nitrogen for 5 minutes. The resultant mix was slowly added to the stirred aqueous solution of polyvinyl pyrrolidone at 22 degrees Centigrade under nitrogen. The temperature was raised to 80 degrees Centigrade with constant agitation and held until polymerization started in approximately 15 minutes, and maintained at 80 degrees Centigrade for an additional 2 hours to complete the reaction. Semi-soft, white opaque beads were collected by filtering off the supernatant liquid and dried to remove any excess water. The beads weighed 450 g for a yield of 90%, and were 0.25 to 0.5 mm in diameter. Other protective colloids such as starch, polyvinyl alcohol, carboxymethyl cellulose, methyl cellulose, or inorganic systems such as divalent alkali metal hydroxides, for example MgOH, may be used in place of the polyvinyl pyrrolidone suspending medium.

In Example III macroporous polymers submicron in size are produced with two or more monomers, at least one monomer of which contains more than a single double bond. The polymerization is conducted in the presence of an active ingredient which does not dissolve or swell the resulting polymer. The monomers and the active ingredient are mutually soluble, but are insoluble in the aqueous suspending medium in which droplets are formed. Polymerization occurs within suspended droplets, and beads or spheres are produced. The active ingredient which is polymerized "in situ" is entrapped and contained within the beads, but the active ingredient is capable of being released. It is also possible to use a volatile liquid during polymerization, and to subsequently thermally drive off the volatile liquid, leaving behind a porous polymer bead product into which a variety of active materials can be subsequently adsorbed.

Examples of polyunsaturated monomers suitable for use in accordance with the present invention are ethylene glycol dimethacrylate, triethylene glycol dimethacrylate, tetraethylene glycol dimethacrylate, trimethylol propane ethoxylated triacrylate, ditrimethylol propane dimethacrylate; propylene, dipropylene and higher propylene glycols, 1,3 butylene glycol dimethacrylate, 1,4 butanediol dimethacrylate, 1,6 hexanediol dimethacrylate, neopentyl glycol dimethacrylate, pentaerythritol dimethacrylate, dipentaerythritol dimethacrylate, bisphenol A dimethacrylate, divinyl and trivinyl benzene, divinyl and trivinyl toluene triallyl maleate, triallyl phosphate, diallyl maleate, diallyl itaconate, and allyl methacrylate. The monounsaturated monomers include allyl methacrylates and acrylates having straight or branched chain alkyl groups with 1 to 30 carbon atoms, preferably 5 to 18 carbon atoms. Preferred monomers include lauryl methacrylate, 2-ethylhexyl methacrylate, isodecylmethacrylate, stearyl methacrylate, hydroxy ethyl methacrylate, hydroxy propyl methacrylate, diacetone acrylamide, phenoxy ethyl methacrylate, tetrahydrofurfuryl methacrylate and methoxy ethyl methacrylate.

As noted previously, the copolymer can be formed by copolymerizing one monounsaturated monomer with one polyunsaturated monomer, or with only polyunsaturated monomers.

EXAMPLE IV

Example I was repeated for each of a series of monomer systems shown in Tables IV-XVII. In each instance, submicron sized copolymeric powders were produced employing a stirring speed of about seventy-five RPM. The catalyst was benzoyl peroxide. Adsorption capacities of the various copolymeric powders for fluids were determined and are shown in the Tables, along with the mole ratios of monomers and the solvent. The abbreviations used in Tables IV-XVII are identified as follows:

| | |
|---|---|
| DAA | Diacetone acrylamide |
| EGDM | Ethylene glycol dimethacrylate |
| TEGDM | Tetraethylene glycol dimethacrylate |
| ST | Styrene |
| DVB | Divinylbenzene |
| VP | Vinyl pyrrolidone |
| IBOMA | Isobornyl methacrylate |
| PEMA | Phenoxyethyl methacrylate |
| IDMA | Isodecyl methacrylate |
| STMA | Stearyl methacrylate |
| HPMA | Hydroxypropyl methacrylate |
| CYMA | Cyclohexyl methacrylate |
| DMAEMA | Dimethylaminoethyl methacrylate |
| TBAEMA | t-butyl aminoethyl methacrylate |
| AMPS | 2-acrylamido propane sulfonic acid |
| BMA | Butyl methacrylate |
| EHMA | 2-ethylhexyl methacrylate |
| MMA | Methyl methacrylate |
| HEMA | 2-hydroxyethyl methacrylate |
| EHO | 2-ethylhexyl oxystearate |
| GG | Glucose glutamate |
| IPA | Isopropyl alcohol |
| PEG | Polyethylene glycol 200 |

TABLE IV

| Monomers | Mole Ratio | Solvent | Adsorption Capacity % | | | |
|---|---|---|---|---|---|---|
| | | | EHO | Glycerine | GG | Water |
| DAA/EGDM | 20/80 | Xylene | 75 | 82 | 83 | 78 |
| DAA/EGDM | 30/70 | Xylene | 77 | 80 | 83 | 78 |
| DAA/EGDM | 40/60 | Xylene | 75 | 75 | 83 | 77 |
| DAA/EGDM | 50/50 | Xylene | 50 | 57 | 67 | 0 |
| DAA/EGDM | 60/40 | Xylene | 40 | 40 | 50 | 0 |
| DAA/TEGDM | 20/80 | Xylene | 40 | 50 | 62 | 58 |
| DAA/TEGDM | 30/70 | Xylene | 29 | 40 | 50 | 55 |
| DAA/TEGDM | 40/60 | Xylene | 25 | 28 | 40 | 43 |
| DAA/TEGDM | 50/50 | Xylene | 25 | 30 | 40 | 43 |
| DAA/TEGDM | 60/40 | Xylene | 22 | 29 | 40 | 40 |

TABLE V

| Monomers | Mole Ratio | Solvent | Adsorption Capacity % | | | |
|---|---|---|---|---|---|---|
| | | | EHO | Glycerine | PEG | Water |
| ST/TEGDM | 20/80 | IPA | 58 | 69 | 69 | 67 |
| ST/TEGDM | 30/70 | IPA | 58 | 64 | 67 | 69 |
| ST/TEGDM | 40/60 | IPA | 62 | 71 | 71 | 61 |
| ST/TEGDM | 50/50 | IPA | 67 | 62 | 54 | 58 |
| ST/TEGDM | 60/40 | IPA | 50 | 58 | 58 | 54 |
| ST/TEGDM | 70/30 | IPA | 50 | 58 | 50 | 54 |
| ST/TEGDM | 80/20 | IPA | 44 | 54 | 50 | 50 |
| ST/DVB | 20/80 | IPA | 80 | 75 | 75 | 0 |
| ST/DVB | 30/70 | IPA | 75 | 67 | 75 | 0 |
| ST/DVB | 40/60 | IPA | 69 | 67 | 67 | 0 |
| ST/DVB | 50/50 | IPA | 64 | 72 | 67 | 0 |
| ST/DVB | 60/40 | IPA | 67 | 71 | 71 | 0 |
| ST/DVB | 70/30 | IPA | 71 | 75 | 76 | 0 |
| ST/DVB | 80/20 | IPA | 50 | 50 | 50 | 0 |

TABLE VI

| Monomers | Mole Ratio | Solvent | Adsorption Capacity % | | | |
|---|---|---|---|---|---|---|
| | | | EHO | Glycerine | GG | Water |
| VP/EGDM | 20/80 | Xylene | 77 | 80 | 74 | 73.6 |
| VP/EGDM | 30/70 | Xylene | 76 | 79 | 78.3 | 70 |
| VP/EGDM | 40/60 | Xylene | 70 | 67 | 75.6 | 75 |
| VP/EGDM | 50/50 | Xylene | 72 | 76 | 80 | 76 |
| VP/EGDM | 60/40 | Xylene | 74 | 80 | 76 | 77 |
| VP/EGDM | 70/30 | IPA | 71 | 78 | 74 | 75 |
| VP/EGDM | 80/20 | IPA | 67 | 75 | 73 | 74 |
| VP/TEGDM | 20/80 | Xylene | 58 | 68.8 | 61.5 | 67.7 |
| VP/TEGDM | 30/70 | Xylene | 70 | 67 | 54.5 | 68.8 |
| VP/TEGDM | 40/60 | Xylene | 54.5 | 61.5 | 52.4 | 64.3 |
| VP/TEGDM | 50/50 | Xylene | 44.4 | 47.4 | 52.4 | 52.4 |
| VP/TEGDM | 60/40 | Xylene | 50 | 44.4 | 50 | 54.4 |
| VP/TEGDM | 70/30 | Xylene | 50 | 47.4 | 44.4 | 50 |
| VP/TEGDM | 80/20 | Xylene | 54.5 | 52.4 | 60 | 58 |

TABLE VII

| Monomers | Mole Ratio | Solvent | Adsorption Capacity % | | | |
|---|---|---|---|---|---|---|
| | | | EHO | Glycerine | GG | Water |
| IBOMA/EGDM | 20/80 | IPA | 62.9 | 9.1 | 71.4 | 0 |
| IBOMA/EGDM | 30/70 | IPA | 64.3 | 16.6 | 67.7 | 0 |
| IBOMA/EGDM | 40/60 | IPA | 68.7 | 28.6 | 61.5 | 0 |
| IBOMA/EGDM | 50/50 | IPA | 67.7 | 16.7 | 58.3 | 0 |
| IBOMA/EGDM | 60/40 | IPA | 50 | 23.1 | 50 | 0 |
| IBOMA/EGDM | 70/30 | IPA | 50 | 9.1 | 47.3 | 0 |
| IBOMA/EGDM | 80/20 | IPA | 52.3 | 16.6 | 44.4 | 0 |
| IBOMA/TEGDM | 20/80 | IPA | 66.6 | 62.9 | 61.5 | 0 |
| IBOMA/TEGDM | 30/70 | IPA | 61.5 | 61.5 | 70.6 | 0 |
| IBOMA/TEGDM | 40/60 | IPA | 64.3 | 64.3 | 71.4 | 0 |
| IBOMA/TEGDM | 50/50 | IPA | 61.5 | 66.6 | 67.7 | 0 |
| IBOMA/TEGDM | 60/40 | IPA | 58.3 | 54.5 | 54.5 | 0 |
| IBOMA/TEGDM | 70/30 | IPA | 47.3 | 50 | 41.1 | 0 |
| IBOMA/TEGDM | 80/20 | IPA | 37.5 | 41.1 | 33.3 | 0 |

TABLE VIII

| Monomers | Mole Ratio | Solvent | Adsorption Capacity % | | | |
|---|---|---|---|---|---|---|
| | | | EHO | Glycerine | GG | Water |
| PEMA/EGDM | 20/80 | IPA | 64.3 | 68.7 | 66.6 | 61.5 |

TABLE VIII-continued

| Monomers | Mole Ratio | Solvent | Adsorption Capacity % | | | |
|---|---|---|---|---|---|---|
| | | | EHO | Glycerine | GG | Water |
| PEMA/EGDM | 30/70 | IPA | 54.5 | 50 | 54.5 | 44.4 |
| PEMA/EGDM | 40/60 | IPA | 52.3 | 47.3 | 72.2 | 9 |
| PEMA/EGDM | 50/50 | IPA | 54.5 | 33.3 | 62.9 | 0 |
| PEMA/EGDM | 60/40 | IPA | 67.7 | 28.5 | 70.5 | 0 |
| PEMA/EGDM | 70/30 | IPA | 69.7 | 44.4 | 60.7 | 0 |
| PEMA/EGDM | 80/20 | IPA | 66.6 | 68.7 | 66.6 | 0 |
| PEMA/TEGDM | 20/80 | IPA | 58.3 | 56.5 | 66.6 | 58.3 |
| PEMA/TEGDM | 30/70 | IPA | 64.2 | 70.5 | 67.7 | 62.9 |
| PEMA/TEGDM | 40/60 | IPA | 66.6 | 67.7 | 71.4 | 69.7 |
| PEMA/TEGDM | 50/50 | IPA | 66.6 | 70.5 | 73.6 | 72.2 |
| PEMA/TEGDM | 60/40 | IPA | 58.3 | 62.9 | 52.3 | 61.5 |
| PEMA/TEGDM | 70/30 | IPA | 50 | 58.3 | 52.3 | 54.5 |
| PEMA/TEGDM | 80/20 | IPA | 67.7 | 73.6 | 76.1 | 47.3 |

TABLE IX

| Monomers | Mole Ratio | Solvent | Adsorption Capacity % | | | |
|---|---|---|---|---|---|---|
| | | | EHO | Glycerine | PEG | Water |
| IDMA/EGDM | 20/80 | IPA | 55 | 64 | 70 | 0 |
| IDMA/EGDM | 30/70 | IPA | 38 | 50 | 44 | 0 |
| IDMA/EGDM | 40/60 | IPA | 50 | 67 | 69 | 0 |
| IDMA/EGDM | 50/50 | IPA | 58 | 64 | 67 | 0 |
| IDMA/EGDM | 60/40 | IPA | 58 | 69 | 69 | 0 |
| IDMA/TEGDM | 20/80 | IPA | 62 | 70 | 70 | 0 |
| IDMA/TEGDM | 30/70 | IPA | 50 | 62 | 62 | 0 |
| IDMA/TEGDM | 40/60 | IPA | 62 | 67 | 67 | 0 |
| IDMA/TEGDM | 50/50 | IPA | 38 | 44 | 50 | 0 |
| IDMA/TEGDM | 60/40 | IPA | 38 | 55 | 50 | 0 |

TABLE X

| Monomers | Mole Ratio | Solvent | Adsorption Capacity % | | | |
|---|---|---|---|---|---|---|
| | | | EHO | Glycerine | PEG | Water |
| STMA/EGDM | 10/90 | IPA | 66 | 64.3 | 66.7 | 0 |
| STMA/EGDM | 20/80 | IPA | 69 | 63 | 65.5 | 0 |
| STMA/EGDM | 30/70 | IPA | 73-75 | 58.3 | 61.5 | 0 |
| STMA/EGDM | 40/60 | IPA | 69-71 | 54.5 | 58.3 | 0 |
| STMA/EGDM | 50/50 | IPA | 60-63 | 52.4 | 52.4 | 0 |
| STMA/TEGDM | 20/80 | IPA | 50 | 47.4 | 52.4 | 0 |
| STMA/TEGDM | 30/70 | IPA | 50 | 64.3 | 50 | 0 |
| STMA/TEGDM | 40/60 | IPA | 52.4 | 61.5 | 58.3 | 0 |
| STMA/TEGDM | 50/50 | IPA | 47.4 | 52.4 | 56.5 | 0 |

TABLE XI

| Monomers | Mole Ratio | Solvent | Adsorption Capacity % | | | |
|---|---|---|---|---|---|---|
| | | | EHO | Glycerine | PEG | Water |
| HPMA/EGDM | 20/80 | Xylene | 64.3 | 61.5 | 61.5 | 9 |
| HPMA/EGDM | 30/70 | Xylene | 54.5 | 16.7 | 58.3 | 0 |
| HPMA/EGDM | 40/60 | Xylene | 54.5 | 9 | 58.3 | 0 |
| HPMA/EGDM | 50/50 | Xylene | 37.5 | 58.3 | 50 | 0 |
| HPMA/EGDM | 60/40 | Xylene | 44.4 | 61.5 | 58.3 | 0 |
| HPMA/EGDM | 70/30 | Xylene | 50 | 44.4 | 37.5 | 0 |
| HPMA/EGDM | 80/20 | Xylene | 61.5 | 16.7 | 58.3 | 0 |
| HPMA/TEGDM | 20/80 | Xylene | 50 | 58.3 | 54.5 | 61.5 |
| HPMA/TEGDM | 30/70 | Xylene | 56.5 | 54.5 | 50 | 60 |
| HPMA/TEGDM | 40/60 | Xylene | 50 | 58.3 | 52.4 | 54.5 |
| HPMA/TEGDM | 50/50 | Xylene | 52.4 | 61.5 | 54.5 | 56.5 |
| HPMA/TEGDM | 60/40 | Xylene | 33.3 | 47.4 | 44.4 | 54.5 |
| HPMA/TEGDM | 70/30 | Xylene | 54.5 | 44.4 | 54.5 | 50 |
| HPMA/TEGDM | 80/20 | Xylene | 50 | 47.4 | 41.2 | 37.5 |

TABLE XII

| Monomers | Mole Ratio | Solvent | Adsorption Capacity % | | | |
|---|---|---|---|---|---|---|
| | | | EHO | Glycerine | PEG | Water |
| CYMA/EGDM | 80/20 | IPA | 61.5 | 71.4 | 66.6 | 0 |
| CYMA/EGDM | 70/30 | IPA | 60 | 66 | 64.2 | 0 |
| CYMA/EGDM | 60/40 | IPA | 61.5 | 66 | 66.6 | 0 |
| CYMA/EGDM | 50/50 | IPA | 64.2 | 66 | 68.7 | 0 |
| CYMA/EGDM | 40/60 | IPA | 64.2 | 66 | 68.7 | 0 |
| CYMA/EGDM | 30/70 | IPA | 61.5 | 66 | 66.6 | 0 |
| CYMA/EGDM | 20/80 | IPA | 66.6 | 71.4 | 75 | 61.5 |

TABLE XII-continued

| Monomers | Mole Ratio | Solvent | Adsorption Capacity % | | | |
|---|---|---|---|---|---|---|
| | | | EHO | Glycerine | PEG | Water |
| CYMA/TEGDM | 80/20 | IPA | 68.7 | 0 | 68.7 | 0 |
| CYMA/TEGDM | 70/30 | IPA | 71.4 | 0 | 69.7 | 0 |
| CYMA/TEGDM | 60/40 | IPA | 66.6 | 0 | 62.9 | 0 |
| CYMA/TEGDM | 50/50 | IPA | | 0 | | 0 |
| CYMA/TEGDM | 40/60 | IPA | 60 | 0 | 72.9 | 0 |
| CYMA/TEGDM | 30/70 | IPA | 64.2 | 0 | 72.2 | 0 |
| CYMA/TEGDM | 20/80 | IPA | 61.5 | 0 | 66.6 | 0 |

TABLE XIII

| Monomers | Mole Ratio | Solvent | Adsorption Capacity % | | | |
|---|---|---|---|---|---|---|
| | | | Water | Mineral Oil | Glycerine | EHO |
| DMAEMA/EGDM | 20/80 | Hexane | 0 | 58.3 | 66.7 | 58.3 |
| DMAEMA/EGDM | 40/60 | Hexane | 66.7 | 61.5 | 70.6 | 66.7 |
| DMAEMA/EGDM | 60/40 | Hexane | 77.3 | 61.5 | 72.2 | 76.2 |
| DMAEMA/EGDM | 80/20 | Hexane | 66.7 | 58.3 | 68.8 | 58.3 |
| TBAEMA/EGDM | 20/80 | Hexane | 0 | 70.6 | 75 | 70.6 |
| TBAEMA/EGDM | 40/60 | Hexane | 0 | 66.7 | 72.2 | 66.7 |
| TBAEMA/EGDM | 60/40 | Hexane | 0 | 61.5 | 68.75 | 61.5 |
| TBAEMA/EGDM | 80/20 | Hexane | 0 | 44.4 | 54.6 | 50 |
| TBAEMA/EGDM | 80/20 | Hexane | 54.6 | 54.6 | 58.3 | 50 |

TABLE XIV

| Monomers | Mole Ratio | Solvent | Adsorption Capacity % | | | |
|---|---|---|---|---|---|---|
| | | | Water | Mineral Oil | Glycerine | EHO |
| AMPS/EGDM | 20/80 | Xylene | 84.3 | 83.3 | 85.3 | 83.3 |
| BMA/EGDM | 20/80 | Hexane | 0 | 70.6 | 75 | 68.8 |
| BMA/EGDM | 40/60 | Hexane | 0 | 70.6 | 77.3 | 70.6 |
| BMA/EGDM | 40/60 | Ethyl-Alcohol | 0 | 66.7 | 73.7 | 68.8 |
| BMA/EGDM | 60/40 | Hexane | 0 | 72.2 | 0 | 73.7 |
| BMA/EGDM | 80/20 | Hexane | 0 | 54.5 | 66.7 | 58.3 |

TABLE XV

| Monomers | Mole Ratio | Solvent | Adsorption Capacity % | | | |
|---|---|---|---|---|---|---|
| | | | Water | Mineral Oil | Glycerine | EHO |
| 2 EHMA/EGDM | 20/80 | IPA | 0 | 68.8 | 66.7 | 64.3 |
| 2 EHMA/EGDM | 30/70 | IPA | 0 | 68.8 | 66.7 | 64.3 |
| 2 EHMA/EGDM | 40/60 | IPA | 0 | 66.7 | 66.7 | 70.6 |
| 2 EHMA/EGDM | 50/50 | IPA | 0 | 64.3 | 68.3 | 61.5 |
| 2 EHMA/EGDM | 60/40 | IPA | 0 | 61.5 | 64.3 | 50 |
| 2 EHMA/EGDM | 70/30 | IPA | 0 | 58.3 | 64.3 | 50 |
| 2 EHMA/EGDM | 80/20 | IPA | 0 | 58.3 | 64.3 | 50 |

TABLE XVI

| Monomers | Mole Ratio | Solvent | Adsorption Capacity % | | | |
|---|---|---|---|---|---|---|
| | | | Water | Mineral Oil | Glycerine | EHO |
| MMA/EGDM | 20/80 | IPA | 61.5 | 58.3 | 64.3 | 58.3 |
| MMA/EGDM | 30/70 | IPA | 64.3 | 61.5 | 66.7 | 61.5 |
| MMA/EGDM | 40/60 | IPA | 61.5 | 64.3 | 64.3 | 61.5 |
| MMA/EGDM | 50/50 | IPA | 58.3 | 54.5 | 61.5 | 58.3 |
| MMA/EGDM | 60/40 | IPA | 54.5 | 50 | 61.5 | 54.5 |
| MMA/EGDM | 70/30 | IPA | 66.7 | 61.5 | 72.2 | 64.3 |
| MMA/EGDM | 80/20 | IPA | 66.7 | 44.4 | 78.3 | 44.4 |

TABLE XVII

| Monomers | Mole Ratio | Solvent | Adsorption Capacity % | | | |
|---|---|---|---|---|---|---|
| | | | Water | PEG | Glycerine | EHO |
| HEMA/EGDM | 20/80 | IPA | 54.5 | 54.5 | 54.5 | 50 |
| HEMA/EGDM | 30/70 | IPA | 58.3 | 64.3 | 58.3 | 54.5 |
| HEMA/EGDM | 40/60 | IPA | 58.3 | 61.5 | 64.3 | 54.5 |
| HEMA/EGDM | 50/50 | IPA | 61.5 | 61.5 | 61.5 | 50 |
| HEMA/EGDM | 60/40 | IPA | 61.5 | 64.3 | 61.5 | 50 |
| HEMA/EGDM | 70/30 | IPA | 58.3 | 64.3 | 58.3 | 50 |
| HEMA/EGDM | 80/20 | IPA | 61.5 | 58.3 | 61.5 | 54.5 |

The water adsorbing porous polymeric materials produced above in some instances are to be contrasted with the water containing beads of U.S. Pat. No. 3,627,708, issued Dec. 14, 1971. The bead of the '708 patent is produced by "in situ" suspension polymerization, and is adapted to contain water only because of the presence of a solubilizer such as sodium bis(2-ethyl hexyl) sulfosuccinate. The materials of Example IV, on the other hand, are produced by a precipitation polymerization process, which contains no solubilizer, and produces a material in the form of a powder consisting of unit particles, agglomerates, and aggregates. Thus, these materials are very distinct from the materials of the '708 patent.

The particulates of the present invention can be used as a carrier and the particulate carrier means can be in the form of micron-sized beads, or the particulate carrier means can be in the form of a powder. In the latter case, the powder constitutes a combined system of particles, the system of powder particles including unit particles of a size less than about one micron in average diameter, agglomerates of fused unit particles of sizes in the range of about twenty to about eighty microns in average diameter, and aggregates of clusters of fused agglomerates of sizes in the range of about two hundred to about twelve hundred microns in average diameter.

As noted above, highly crosslinked, polymeric systems consisting of particles of submicron size, can be prepared from monomers having at least two polymerizable unsaturated bonds and containing no comonomers having monounsaturated moiety. These highly crosslinked systems can adsorb large quantities of active substances even of very different structures and properties.

Examples of such monomers are bis or poly acrylates, methacrylates or itaconates of ethylene glycol, propylene glycol, di-, tri-, tetra-, poly- ethylene glycol and propylene glycol, trimethylol propane, glycerine, erythritol, xylitol, pentaerythritol, di-pentaerythritol, sorbitol, mannitol, glucose, sucrose, cellulose, hydroxy cellulose, methyl cellulose, and 1,2; and 1,3- propanediol, 1,3; and 1,4-butanediol, 1,6-hexanediol, 1,8-octanediol, and cyclohexanediol, and triol.

Similarly, bis acrylamido or methacrylamido compounds can be used, such as methylene bis acryl or methacrylamide, 1,2-dihydroxy ethylene bis-acryl or methacrylamide, and hexamethylene bis-acryl or methacrylamide.

Another group of monomers are represented by di or poly vinyl esters such as divinyl oxalate, malonate, succinate glutarate, adipate, sebacate, divinyl maleate, fumarate, citraconate, and mesaconate.

Still another group of monomers is represented by di or poly vinyl ethers of ethylene, propylene, butylene, glycols of glycerine, pentaerythritol, sorbitol, divinyl ether, di or poly-allyl compounds based on glycols, and glycerine, or combinations of vinyl allyl or vinyl acryloyl compounds such as vinyl methacrylate, acrylate, allyl methacrylate, acrylate, and methallyl methacrylate, acrylate.

Aromatic, cycloaliphatic or heterocyclic monomers such as divinyl benzene, toluene, diphenyl, cyclohexane, trivinyl benzene, divinyl pyridine, and piperidine, can also be used.

The polymerization is achieved by the use of a variety of free radical initiators which can be azo compounds, a peroxy dicarbonate, a peroxy ester, or a sulfonyl acid peroxide. Illustrative of free radical initiators in the process are 2,2'-azobis(2,4-dimethyl-4-methoxy valeronitrile), benzoyl peroxide, 2,2'-azobis-(2,4-dimethylvaleronitrile), 2,2'-azobis (isobutyronitrile), 2-t-butylazo-2-cyano-4-methoxy-4-methylpentane, acetyl peroxide, 2-t-butylazo-2-cyano-4-methylpentane, 2,4-dichlorobenzoyl peroxide, p-chlorobenzoyl peroxide, decanoyl peroxide, diisononanyl peroxide, lauroyl peroxide, propinoyl peroxide, bis(4-t-butyl cyclohexyl) peroxy dicarbonate, di(sec-butyl) peroxy dicarbonate, diisopropyl peroxy carbonate, di(n-propyl) peroxy carbonate, di(2-ethylhexyl) peroxy carbonate, di(2-phenoxyethyl) peroxy carbonate, t-amyl peroxy pivatate, t-amyl perpivatate, t-butyl peroxyacetate, t-butyl peroxyisobutyrate, t-butyl peroxypivalate, t-butyl peroxy neodecanonate, t-amyl perneodecanonate, cumyl perneodecanonate, cumyl perpivate, 2,5-dimethyl-2,5-bis(2-ethyl hexanoyl peroxy) hexane, t-butylperoxy-2-ethylhexanoate, t-amyl peroxy (2-ethylhexanoate) and acetyl cyclohexyl sulfonyl peroxide.

Illustrative redox initiators are methylbutyl amine, bis(2-hydroxyethyl)butyl amine, butyldimethyl amine, dimethyl amine, dibenzylethyl amine, diethylmethyl amine, dimethylpentyl amine, diethyl amine, 2,2',2"-trihydroxy dipropyl ethyl amine, di-n-propylene amine, 2,2',2"-trimethyl tributyl amine, triethyl amine, dimethyl aminoacetal, pentylhexyl amine, triethanolamine, trihexyl amine, trimethyl amine, trioctadecyl amine, tripropyl amine, trisopropyl amine, tetramethylene diamine, and esters of para-amino benzoic acid, e.g., p-dimethyl amino-2-ethylhexyl-benzoate, dimethyl aminoethyl acetate, 2-(n-butoxy)ethyl 4-dimethylaminobenzoate, 2-(dimethylamino) ethyl benzoate, ethyl-4 dimethylaminobenzoate, methyldiethanolamine, dibutyl amine, N,N-dimethylbenzylamine, methylethyl amine and dipentyl amine.

The following examples and tables illustrate the novel cleaning process of the present invention. Table XVIII lists a number of common stains and solvent or chemical treatments that may be empolyed to remove such stains in accordance with the present invention.

TABLE XVIII

| STAIN | SOLVENT OR CHEMICAL TREATMENT |
| --- | --- |
| Tea | Ammonia |
| Coffee | Soap, dithionate |
| Cocoa | Soap, hydrocarbon emulsion |
| Chocolate | Soap, hydrocarbon emulsion |
| Milk, sour cream, yogurt | Hydrocarbon, ammonia |
| Beer | Acetic acid, hydrogen peroxide |
| Liquors | Enzyme, ammonia |
| Wine | Ammonia, alcohol, borax |
| Honey | Enzyme |
| Fruit juices | Enzyme, ammonia |
| Eggs | Water, soap, hydrocarbons |
| Red cabbage, beet root | Ammonia, dithionate |
| Vegetable and original oils | Organic solvents |

TABLE XVIII-continued

| STAIN | SOLVENT OR CHEMICAL TREATMENT |
|---|---|
| Gravies | Hydrocarbon-emulsions, ammonia |
| Mustard | Glycerine, formic acid |
| Lipstick | Hydrocarbon emulsion, ethylalcohol |
| Various cosmetics | Ammonia, hydrocarbons, detergents |
| Nail lacquer | Butylacetate |
| Permanent wave | Hydrofluoric acid |
| Hair dyes | Citric acid, hydrofluoric acid |
| Henna | Glycerine |
| Fragrances | Hydrocarbon emulsion, alcohol |
| Toothpaste | Water |
| Castor Oil | Ethylalcohol, acetic acid |
| Fish oil | Hydrocarbon emulsion |
| Vaseline | Hydrocarbon, oxalic acid |
| Ointments | Hydrocarbons, acetic or formic acid |
| Iodine | Thiosulfate, hydrogen peroxide, acetic acid |
| Potassium hypermanganate | Sodium persulfite |
| Silver nitrate | Potassium iodide |
| Red or green ink | Glycerine, ammonia |
| Blue or black ink | Glycerine, ammonia, lacte, hydrofluoric acid |
| Rubber stamp ink | Glycerine and alcohol, hydrogen peroxide |
| Typing ribbon | Hydrocarbon emulsion |
| Nitrocellulose, cellulose acetate | Butylacetate, acetone, hydrocarbon |
| Vegetable adhesives | Ammonia, ethylalcohol, water |
| Photographic Developer | Thiosulfate, ammonia, hydrogen peroxide |
| Waxes, paraffin | Organic solvents |
| Fungus | Ammonia, hydrogen peroxide |
| Shoe polish | Hydrocarbon emulsion |
| Perspiration stains | Ammonia, acetic acid, ethylalcohol, hydrogen peroxide |
| Blood | Hydrogen peroxide, enzyme |
| Urine | Acetic acid |
| Rust | Oxalic acid, tin chloride |
| Grass, vegetables | Hydrocarbon emulsion, ethylalcohol |

The disadvantgae of conventional treatments is that the solvent dissolving the stain spreads, carrying the stain and depositing the diluted stain in the form of concentric rings. Thus, the textile has to be washed in the solvent to remove the stain entirely. When the macroporous copolymers of this invention are used as cleaning aids ehis phenomena does not occur. Instead, the polymer adsorbs the dissolved stain leaving no concentric rings. After evaporation of the solvent from the polymer, the staining agent remains on the polymer. To complete the cleaning, the dry polymer is removed by brushing.

The copolymers can also be used to remove stains from solid substrates such as glass, metals, lacquers, and wood, without using solvents or other chemicals which can cause deterioration of the substrate. Such treatment includes greasy and fatty viscous deposits. Simply dusting the deposit of vaseline or tar, followed by mixing and rubbing, removes the deposit as a plastic mass.

EXAMPLE V

A cotton textile was stained with a drop of used motor oil and the oil was allowed to soak into the textile. The copolymer powder of Example I was mixed with heptane to a content of eighty percent by weight of the solvent. The copolymer powder containing the entrapped solvent was pressed onto the oil stained textile surface. The stain was absorbed into the powder within about five minutes and the powder was removed from the surface with a brush. No concentric rings were observed.

EXAMPLE VI

Example V was repeated employing the copolymer powder of Example I produced with a polyunsaturated monomer of tetraethylene glycol dimethacrylate. Identical results were observed.

EXAMPLE VII

Examples V and VI were repeated with a chlorophene solvent and identical results were observed.

EXAMPLE VIII

Cotton, silk, and artificial silk sample swatches were stained with strawberry jelly, and sweet and sour sauce. The powder of Example I was mixed with twenty weight percent water solution of a nonionic surface active agent TRITON X-100. The powder was loaded to a content of about eighty weight percent of the solvent. The powder containing the entrapped solvent was pressed into each of the stained areas of the various swatches. At the end of five minutes, the powder was removed from each swatch with the assistance of pressurized air without a trace of concentric rings.

EXAMPLE IX

Example VIII was repeated with the powder of Example VI containing eighty weight percent of water. Similar results were observed.

EXAMPLE X

The powder of Example I was loaded with solvent and various stains and substrates were treated in accordance with the foregoing procedures. The solvents employed were heptane and methylene chloride. In each case no rings were observed when the powder was removed from the sample surface being treated. The treated surfaces and the staining agents are shown below in Table XIX.

TABLE XIX

| Stain | Surface |
|---|---|
| Butter | wool |
| Butter | paper |
| Mineral Oil | paper |

TABLE XIX-continued

| Stain | Surface |
| --- | --- |
| Grass* | cotton |
| Used motor oil | wool |
| Used motor oil | silk |
| Used motor oil | rayon |
| Used motor oil | acetate silk |
| Used motor oil | linen |
| Used motor oil | nylon |
| Used motor oil | polyester 60% cotton 40% |
| Used motor oil | polyester 100% |

*Ethyl/alcohol solvent

EXAMPLE XI

A glass plate was covered with a silicone grease. The powder of Example I was dusted onto the plate and mixed with the grease. The powder absorbed the grease forming a plastic-like mass which was easily removed from the glass surface leaving a clean plate. Identical results were observed employing hydrocarbon greases and waxes.

EXAMPLE XII

Spectacle lenses soiled by lipid deposits were cleaned in accordance with the procedure of Example XI. The lenses were flushed with water completely removing the lipid deposits from the surfaces of the spectacle lenses. Identical results were obtained employing the powder of Example VI. In either case, the powder did not adhere to the bifocal or trifocal lines of the spectacle lenses treated.

EXAMPLE XIII

The powder of Example I and the powder of Example VI were used to clean dentures. Dentures covered by plaque were dusted with the powders, rubbed, and flushed with water. In each case, the plaque was removed from the denture surfaces treated.

While the foregoing disclosure specifies various uses of the materials of the present invention, as well as various types and compositions of ingredients which may be entrapped within these and similar materials, the patent literature is replete with uses and ingredients which may be entrapped in these and similar materials. For example, U.S. Pat. No. 4,690,825, discloses as active ingredients lubricants, emollients, moisturizers, pigments, insect or flea repellents, fragrances, vitamins, and drugs. When the active ingredient is a drug, it is said to include anti-infectives such as antibiotics, fungicides, scabicides, pediculicides, iodine, anti-inflammatory agents, antipruritics, astringents, anti-hidrotics, keratolytic agents, caustics, keratoplastic agents, rubefacients, sunscreens, demukents, protectants, and detergents. Uses of loaded beads includes cosmetic preparations such as hand creams, acne products, deodorants, antiperspirants, baby powders, foot powders, body powders, lip ices, lip sticks, baby creams and lotions, mouthwashes, dentifrices, medicated facial creams and lotions, shampoos, shaving creams, pre- and after-shave lotions, depilatories, and hairgrooming preparations.

U.S. Pat. No. 4,724,240, names as active ingredients ethylhexyl oxystearate, arachidyl propionate, ethylhexyl adipate, isopropyl myristate, ethanol, stearyl alcohol, propylene glycol, propionic acid, stearic acid, polyoxypropylene cetyl alcohol, carbowax, polyethylene glycol, petroleum jelly, mineral oil, mineral spirits, lanolin, acetylated lanolin, isopropyl lanolate, hexamethyldisiloxane, cyclic polydimethylsiloxanes, polyphenylmethylsiloxanes, polydimethyl-trimethylsiloxanes; phenyl, ethyl, and vinyl-substituted polysilanes; and cosmetic dyes. Materials loaded with such ingredients are said to be useful in cosmetic, beauty, toiletry, and healthcare products, insecticides, disinfectants, flavors, perfumes, antiperspirant wax or oil base sticks, deodorants, colognes, pressed powders, and toilet soaps.

Entrapped functional materials in the Published European Application No. 0252463A2 are said to encompass pigments, perfumes, pheromones, synthetic insect attractants, pesticides including juvenile hormone analogs, herbicides, pharmaceuticals, antimicrobial agents, sunscreens, light stabilizers, fragrances, flavors including sweeteners, and various chemicals. Of the various chemicals disclosed are menthol, soybean oil, Vitamin E, salicylic acid, squalane, simethicon, bromochlorinated paraffin, benzophenone, petroleum distillate, jojoba oil, and citrus oil. The published application also specifically identifies and names four pheromones, twenty pesticides, twenty-three fragrances, about thirty-seven chemicals, and some twenty-two emollients, that may be entrapped in the materials as active ingredients.

In the Patent Cooperation Treaty International Publication No. WO/88/01164, there is also listed as specifically named ingredients which may be loaded into the beads approximately twenty-two ultraviolet absorbers, nineteen insect repellants, and thirty emollients. The publication also names several steroids including adrenocortical steroids such as fluocinolone, fluocinolone acetonide, triamcinolone acetonide, beta-methasone valerate, timobesone acetate, hydrocortisone, hydrocortisone acetate, triamcinolone, prednisolone, prednisolone acetate, dexamethasone, beclomethasone dipropionate, betamethasone diproprionate, betamethasone benzoate, clocorolone pivalate, halcinonide, flumethasone pivalate, and desonide.

European Published Application No. 0306236A2, published Mar. 3, 1989, discloses "in situ" and "post absorbed" suspension polymerized beads loaded with six different categories of active ingredients. The six categories of active ingredients are hair growth promoters, acne treatments, fragrances, vitamins, pain relievers, and epidermal lipid substitutes. The hair growth promoter is Minoxidil. For acne treatment there is employed benzoyl peroxide, salicylic acid, and resorcinol. Fragrances include flower oils, essential oils, animal and synthetic fragrances, and resinoids. Some thirty-nine specific fragrances are named. Vitamins include A, D, E, K, B1, B2, B12, B15, B17, C, niacin, folic acid, pantothenic acid, biotin, bioflavinoids, choline, inositol, and 'F. Cod liver oil and retinoids are also disclosed. Some twenty-two pain relievers, and some twenty-two mixtures and combinations of various pain relievers are disclosed, among which are menthol, camphor, and methyl salicylate. The epidermal lipid substitutes are squalane and squalene. The six categories of loaded beads may be used along or as topical applications in creams, ointments, lotions, and oils. In addition, the fragrance loaded beads can be added to perfumes, colognes, cosmetics, soaps, paper products, detergents, and body and foot powders. The vitamin loaded beads also find application in lip balms, lipsticks, eye shadows, foundations, and blushers.

In U.S. Pat. No. 4,719,040, issued Jan. 12, 1988, a porous polymer powder laden with perfume is included as an ingredient in an aqueous air freshener gel. U.S. Pat. No. 4,764,362, issued Aug. 16, 1988, and a divisional thereof U.S. Pat. No. 4,813,976, issued Mar. 21, 1989, relate to emery boards including an emollient entrapped onto a absorbent acrylates copolymer powder. Filing of a nail releases the emollient which conditions and lubricates the nails and cuticles. A toothpaste containing dental flossing tape is disclosed in U.S. Pat. No. 4,776,358, issued Oct. 11, 1988. Included as an ingredient of the dentifrice are "microsponges" containing a flavor oil. In U.S. Pat. No. 4,828,542, issued May 9, 1989, copolymer bead and powder particles entrapping various functional materials are bonded to the surfaces of a reticulated polyurethane foam. Among the enumerated functional materials which may be entrapped are adhesives; pharmaceuticals such as insulin, interferon, albumin, hormones, and monoclonal antibodies; flavors; fragrances for perfume samplers, air fresheners, and drawer liners; colors; inks; liquid crystals; oils; waxes; solvents; resins; fire extinguishing agents; insect repellants for mothballs, and flea and tick applications; agricultural chemicals such as insecticides, fungicides, and pheromones; disinfectants; cosmetics such as skin lotions, hair care products, sunscreens, and mouth wash; vitamins; antiperspirants; contraceptives; medicants such as Benzocaine, transdermal drugs, analgesics, allergy bacteria, methyl salicylate, and nitroglycerin. Molded and layered articles are also disclosed.

It will be apparent from the foregoing that many other variations and modifications may be made in the structures, compounds, compositions, and methods described herein without departing substantially from the essential features and concepts of the present invention. Accordingly, it should be clearly understood that the forms of the invention described herein are exemplary only and are not intended as limitations of the scope of the present invention.

That which is claimed is:

1. A method of removing a stain from a surface comprising applying to the surface particles of a highly crosslinked hydrophobic macroporous polymer, the particles having entrapped therein a solvent for the stain, dissolving the stain with the solvent, adsorbing the stain and the solvent into the particles, and removing the particles containing the stain and the solvent from the surface, the polymer being in the form of unit particles, agglomerates and aggregates, the unit particles being less than one micron in average diameter, the agglomerates being fused unit particles and having an average diameter in the range of 20-80 microns, and the aggregates being fused agglomerates and having an average diameter in the range of 200-1200 microns.

2. The method of claim 1 in which the polymer is formed from lauryl methacrylate and one polyunsaturated monomer selected from the group consisting of ethylene glycol dimethacrylate and tetraethylene glycol dimethacrylate.

3. The method of claim 1 including the step of evaporating the solvent from the particles and discarding the solvent free particles containing the stain.

4. The method of claim 1 in which the surface is a textile selected from the group consisting of wool, cotton, silk, rayon, linen and polyester.

5. The method of claim 1 in which the solvent is selected from the group consisting of heptane, methylene chloride, ethyl alcohol and chloroprene.

6. A method of removing a stain from a surface comprising applying to the surface particles of a highly crosslinked hydrophobic macroporous polymer, rubbing the particles into the stain, absorbing the stain into the particles, and removing the particles containing the stain from the surface, the polymer being in the form of unit particles, agglomerates and aggregates, the unit particles being less than one micron in average diameter, the agglomerates being fused unit particles and having an average diameter in the range of 20-80 microns, and the aggregates being fused agglomerates and having an average diameter in the range of 200-1200 microns.

7. The method of claim 6 in which the polymer is formed from lauryl methacrylate and one polyunsaturated monomer selected from the group consisting of ethylene glycol dimethacrylate and tetraethylene glycol dimethacrylate.

8. The method of claim 6 in which the surface is a spectacle lens.

9. The method of claim 8 in which the stain is a lipid deposit.

10. The method of claim 6 in which the surface is a denture.

11. The method of claim 10 in which the stain is plaque.

* * * * *